US011759373B2

(12) United States Patent
Bäck et al.

(10) Patent No.: US 11,759,373 B2
(45) Date of Patent: *Sep. 19, 2023

(54) METHOD OF PRODUCING A CHASSIS WEB WITH A WAISTBAND COMPONENT AND DISPOSABLE PANT ARTICLE PRODUCED FROM THE CHASSIS WEB

(71) Applicant: Essity Hygiene and Health Aktiebolag, Gothenburg (SE)

(72) Inventors: Lucas Bäck, Gothenburg (SE); Karin Ljungberg, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 280 days.

This patent is subject to a terminal disclaimer.

(21) Appl. No.: 17/085,220

(22) Filed: Oct. 30, 2020

(65) Prior Publication Data
US 2021/0045932 A1 Feb. 18, 2021

Related U.S. Application Data

(63) Continuation of application No. 15/758,564, filed as application No. PCT/SE2015/000057 on Sep. 9, 2015, now Pat. No. 11,020,282.

(51) Int. Cl.
*A61F 13/15* (2006.01)
*B32B 38/00* (2006.01)
(Continued)

(52) U.S. Cl.
CPC .. *A61F 13/15804* (2013.01); *A61F 13/15691* (2013.01); *A61F 13/15723* (2013.01);
(Continued)

(58) Field of Classification Search
CPC .......... A61F 13/49011; A61F 13/49012; A61F 13/15723; A61F 13/15691; A61F 13/15804; B32B 38/0004; Y10T 156/1057
See application file for complete search history.

(56) References Cited

U.S. PATENT DOCUMENTS 7,160,408 B2 1/2007 Otsubo
8,545,654 B2 10/2013 Lakso et al.
(Continued)

FOREIGN PATENT DOCUMENTS

CN 101222893 A 7/2008
CN 102245145 A 11/2011
(Continued)

OTHER PUBLICATIONS

European Search Report issued in corresponding European Patent Application No. 20187861.8, dated Oct. 29, 2020 (8 pages).
(Continued)

*Primary Examiner* — George R Koch
*Assistant Examiner* — Christopher C Caillouet
(74) *Attorney, Agent, or Firm* — BUCHANAN INGERSOLL & ROONEY PC

(57) ABSTRACT

A method for producing a chassis web for a disposable pant article, the method including feeding a first continuous base web in a machine direction; attaching a continuous elastic waistband component to the first base web in an attachment area extending in the machine direction; attaching a second continuous base web to the first continuous base web and the continuous waistband component, covering at least the continuous waistband component, thereby forming a compound base web having first and second side edges, the attachment area being spaced apart from at least one of the first and second side edges of the compound base web; severing the compound base web and the attached waistband component by cutting; shifting positions of the first panel web and the second panel web in a cross machine direction; forming a coherent chassis web.

12 Claims, 4 Drawing Sheets

(51) Int. Cl.
*A61F 13/496* (2006.01)
*A61F 13/49* (2006.01)

(52) U.S. Cl.
CPC ...... *A61F 13/496* (2013.01); *A61F 13/49011* (2013.01); *A61F 13/49012* (2013.01); *A61F 2013/15869* (2013.01); *B32B 38/0004* (2013.01); *Y10T 156/1057* (2015.01)

(56) References Cited

U.S. PATENT DOCUMENTS

| | | | |
|---|---|---|---|
| 10,201,458 B2 | 2/2019 | Carlson et al. | |
| 11,020,282 B2* | 6/2021 | Bäck | A61F 13/15804 |
| 11,399,987 B2* | 8/2022 | Bäck | A61F 13/15723 |
| 2003/0028166 A1 | 2/2003 | Price et al. | |
| 2006/0030831 A1 | 2/2006 | Matsuda et al. | |
| 2006/0059598 A1* | 3/2006 | Lohoff | A61F 13/49017 2/69 |
| 2008/0108964 A1 | 5/2008 | Edwall | |
| 2008/0141839 A1* | 6/2008 | Van Gompel | A61F 13/495 29/428 |
| 2008/0177242 A1 | 7/2008 | Chang | |
| 2009/0275911 A1 | 11/2009 | Hormung et al. | |
| 2010/0292663 A1* | 11/2010 | LaVon | A61F 13/49019 604/386 |
| 2014/0005019 A1 | 1/2014 | Hargett et al. | |
| 2014/0005628 A1 | 1/2014 | Lavon et al. | |
| 2015/0119219 A1* | 4/2015 | Sina | A61F 13/15699 493/343 |
| 2015/0164700 A1 | 6/2015 | Schwartz | |
| 2016/0270971 A1* | 9/2016 | Raycheck | A61F 13/49001 |
| 2017/0196738 A1* | 7/2017 | Manabe | A61F 13/49 |
| 2018/0250171 A1 | 9/2018 | Bäck et al. | |

FOREIGN PATENT DOCUMENTS

| | | |
|---|---|---|
| EP | 2380540 A1 | 10/2011 |
| EP | 3162331 A1 | 5/2017 |
| JP | 2004187873 A | 7/2004 |
| JP | 2006001167 A | 1/2006 |
| JP | 2007181543 A | 7/2007 |
| JP | 2009536865 A | 10/2009 |
| WO | 03047488 A1 | 6/2003 |
| WO | 2005122985 A1 | 12/2005 |
| WO | 2007133127 A1 | 11/2007 |
| WO | 2007133146 A1 | 11/2007 |
| WO | 2007138373 A1 | 12/2007 |
| WO | 2008079061 A1 | 7/2008 |
| WO | 2013005788 A1 | 1/2013 |
| WO | 2015198967 A1 | 12/2015 |

OTHER PUBLICATIONS

First Office Action dated Nov. 30, 2021, by the Chinese Patent Office in corresponding Chinese Patent Application No. 202110388707. 4, and an English Translation of the Office Action. (22 pages).

Search Report and Written Opinion dated Mar. 14, 2020 by the Brazilian Patent Office in corresponding Brazilian Patent Application No. BR112018003356-1, English Translation only, (4 pages).

Extended European Search Report dated Mar. 8, 2019, issued by the European Patent Office in corresponding European Application No. 15903696.1-1102, (5 pages).

Office Action (Notice of Reasons for Rejection) dated Mar. 18, 2019, by the Japanese Patent Office in corresponding Japanese Patent Application No. 2018-512549, and an English Translation of the Office Action. (11 pages).

Office Action (Notice of Reasons for Refusal) dated Mar. 18, 2019, by the Japanese Patent Office in corresponding Japanese Patent Application No. 2018-512618, and an English Translation of the Office Action. (12 pages).

International Preliminary Report on Patentability (Form PCT/IPEA/409) dated Jan. 30, 2018, by the European Patent Office, in International Application No. PCT/SE2015/000056, (15 pages).

International Preliminary Report on Patentability (Form PCT/IPEA/409) dated Jan. 30, 2018, by the European Patent Office, corresponding in International Application No. PCT/SE2015/000057, (15 pages).

International Search Report (PCT/ISA/210) dated May 31, 2016, by the Swedish Patent Office as the International Searching Authority for International Application No. PCT/SE2015/000057.

Written Opinion (PCT/ISA/237) dated May 31, 2016, by the Swedish Patent Office as the International Searching Authority for International Application No. PCT/SE2015/000057.

Written Opinion (PCT/IPEA/408) dated Sep. 19, 2017, by the Swedish Patent Office as the International Preliminary Examining Authority for International Application No. PCT/SE2015/000057.

Written Opinion (PCT/IPEA/408) dated Nov. 23, 2017, by the Swedish Patent Office as the International Preliminary Examining Authority for International Application No. PCT/SE2015/000057.

* cited by examiner

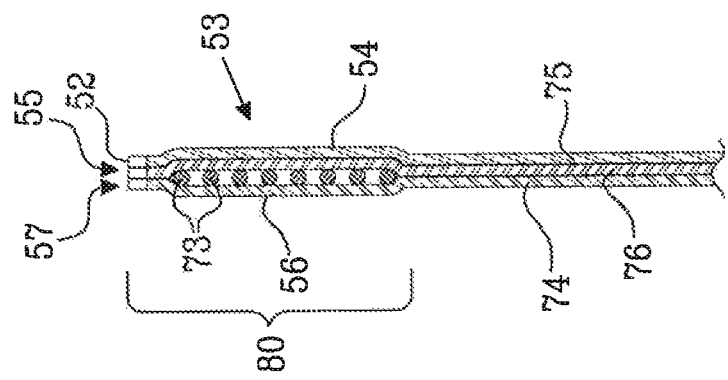
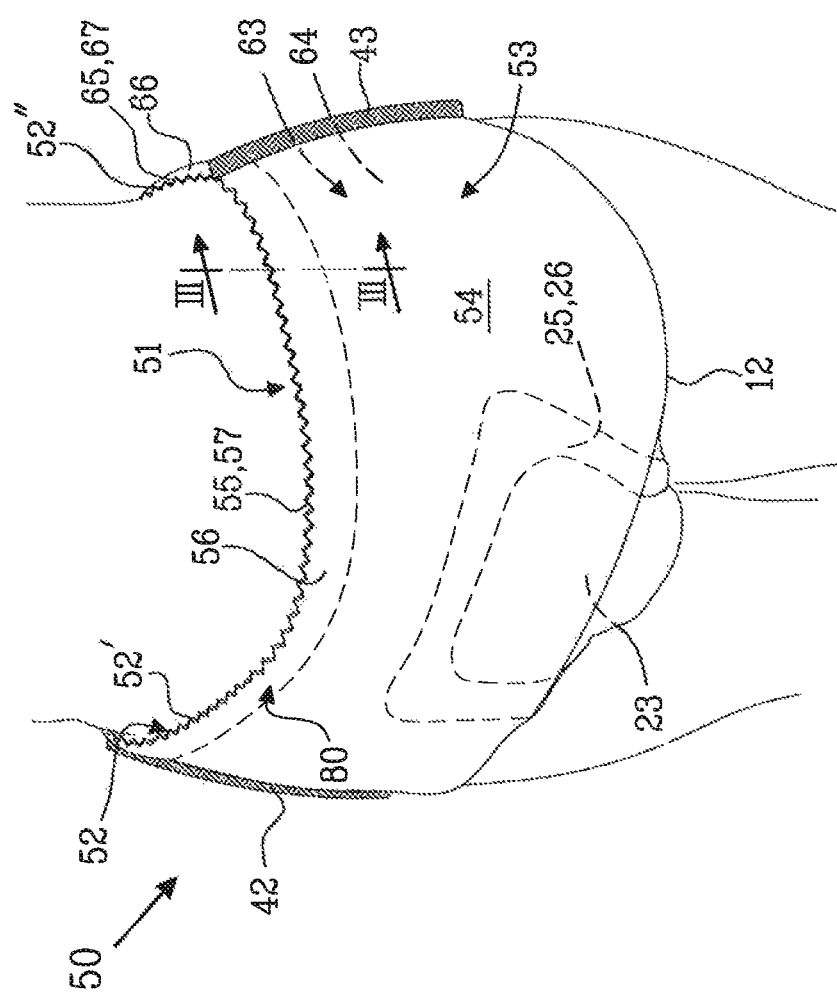
Fig.3
Fig.2

METHOD OF PRODUCING A CHASSIS WEB WITH A WAISTBAND COMPONENT AND DISPOSABLE PANT ARTICLE PRODUCED FROM THE CHASSIS WEB

CROSS-REFERENCE TO RELATED APPLICATIONS

The present application is a continuation of U.S. Ser. No. 15/758,564, filed in the United States on Mar. 8, 2018, and which is a national stage application of PCT/SE2015/000057, filed in Sweden on Sep. 9, 2015. The subject matter of U.S. Ser. No. 15/758,564 and PCT/SE2015/000057 is incorporated herein by reference.

TECHNICAL FIELD

The invention pertains to a method for producing a chassis web for a disposable pant article, and a pant article produced according to the method.

BACKGROUND

Disposable pant articles are articles which are designed to fit like a pair of underpants about the lower torso of a wearer. A disposable pant article may comprise absorbent material integrated in the article. A common type of disposable pant article is a disposable absorbent pant article which includes a pant-shaped chassis and an absorbent core component integrated with the chassis. Such articles are intended to fit comfortably and snugly about the wearer and to be as similar in feel and fit to regular underwear as possible. It is further desirable that the articles are capable of being pulled up and down over the hips of the wearer to allow the wearer or caregiver to easily put on and remove the article when it has been soiled. In some instances, disposable pant articles are provided with means for easy breaking or opening of side seams to allow a used article to be removed without being pulled down over the wearer's legs. The pant articles may be provided with fastener elements allowing them to be opened and reclosed, thus offering the option of putting on or taking off the article either as a pair of regular panties or in the manner of an open diaper.

Pant absorbent articles, in which portions of the chassis are composed of an elastic laminate comprising first and second layers of fibrous material and an elastic film layer located there between, are known through for example WO 2005/122985 and WO 2007/133127. A chassis composed of elastic laminates of this type may be relatively smooth and more underwear-like with fewer wrinkles as compared to laminates comprising elastic strands sandwiched between fibrous materials, as disclosed in for example US 2003/0028166 and US 2009/0275911.

The pant articles are generally provided with an elastic waistband which provides enhanced fit in a wearer's waist and hip area. The waistband may be attached as a separate component to an edge of a rear body panel and/or a front body panel of the pant article. Although a construction of this kind with a cantilevered waistband provides great freedom with regard to the construction, shape and choice of materials for the waistband, it has been found that the bond strength in the join between the waistband and the body panel may be insufficient resulting in the join being subject to rupturing when pulling on the pant article.

Accordingly, it is an object to offer an improved manufacturing process for attaching an elastic waistband. It is also an object to offer a simplified process for attaching an elastic waistband. It is a further object to offer a pant article with improved comfort and appearance.

SUMMARY

The above objects may be achieved with a method as disclosed herein.

As set out herein, there is offered a method for producing a chassis web which may be further processed into a disposable pant article, in accordance with claim 1. A pant article in accordance with claim 20 may be obtained from the chassis web produced by the methods as disclosed herein. Further embodiments are set out in the dependent claims.

Disclosed herein is a method for producing a chassis web for a disposable pant article, the method comprising:

feeding a first continuous base web in a machine direction MD, the first continuous base web having first and second side edges extending in the machine direction MD;

attaching a continuous waistband component to the first base web in an attachment area, the attachment area extending in the machine direction MD and being arranged between the first and the second side edges of the first base web;

attaching a second continuous base web to the first continuous base web and the continuous waistband component, covering at least the continuous waistband component, the second continuous base web having first and second side edges extending in the machine direction MD thereby forming a compound base web having first and second side edges, the attachment area being spaced apart from at least one of the first and the second side edges of the compound base web;

severing the compound base web and the attached elastic waistband component by cutting along a cutting line extending through the attachment area in the machine direction MD thereby creating a first panel web having a first side edge and comprising a first panel portion and a first waistband portion and a second panel web having a second side edge and comprising a second panel portion and a second waistband portion, the first panel web and the second panel web extending in the machine direction MD with the first and second waistband portions facing each other in a side-by-side arrangement;

shifting positions of the first panel web and the second panel web in a cross machine direction CD perpendicular to the machine direction MD, thereby bringing the first and the second panel webs into an arrangement with first and second cut edges facing away from each other in the cross machine direction CD and with the first and second side edges of the first and second panel webs facing each other in the cross machine direction CD;

directly or indirectly connecting the first side edge of the first panel web with the second side edge of the second panel web thereby forming a coherent chassis web.

The first and second base webs may be the same or different types of webs, selected among elastic webs and non-elastic webs such as non-elastic nonwoven webs, elastic nonwoven webs, elastified nonwoven webs elastic and non-elastic polymeric films and laminate webs comprising two or more layers of such materials. The second continuous base web may be coextensive with the first continuous base web. Alternatively, the first and second base webs may have different widths and/or may be joined with each other in a completely overlapping configuration, implying that the side edges of the first and second base webs may not coincide or may coincide only along one side edge of the compound base web. The width of the compound base web is defined between the side edges of the compound base web. When the first and second base webs have different widths or when they are attached to each other in an only partly overlapping configuration, the compound base web has at least one side edge portion defined by only one of the first and second base webs.

The severing step produces two web parts constituting the first panel web and the second panel web which each comprises a portion of the base web and a portion of the waistband component and which each has a cut edge formed by simultaneously cutting through both the base web and the waistband component such that immediately after the severing step, the cut edge on the first panel portion completely matches the cut edge on the second panel portion. This also implies that the base web and the waistband on each of the panel webs have a joint cut edge produced by the severing step. The joint cut edge provides a pant article produced from the chassis web with a comfortable, functional and neat waist border without any layer of the waist border material protruding past any other layer of the waist border material.

The shifting step may be performed by translating one or both of the first panel web and the second panel web in the cross machine direction. The shifting step may involve shifting the panel webs also in the machine direction as the shifting step may be carried out by guiding a translated web portion along a longer travelling path than the other web portion. By way of example, a translated web portion may be guided over one or more shifting rollers and/or over one or more shifting plates. Consequently, when the web portions have been shifted in the cross machine direction and are again brought into parallel alignment with each other, they may also have been displaced in the machine direction. This means that the waistband on a pant article produced from the chassis web may have a front waistband cut edge which not at all or only partly originates from the same portion of the waistband component as the rear waistband cut edge.

The elastic waistband component may be attached to the first base web in a position where it is placed along one of the side edges of the compound base web. Severing the compound base web and the elastic waistband component produces a first panel web having the panel portion and the waistband portion arranged in a completely overlapping configuration while the second panel web has a waistband portion which overlaps with only an edge part of the panel portion. The first panel web may be shifted and attached as a waistband along the edge of the second panel web which is opposite to the edge part of the second panel web which overlaps with the waistband portion of the second panel web.

The coherent chassis web produced according to the method as disclosed herein may be an intermediate article which is rolled up and which can be stored and transported in the rolled-up state for later use as a component in a pant forming process. Alternatively the coherent chassis web may be further processed in-line and directly converted into individual pant articles The compound base web has a width W between the first and the second side edges of the compound base web and the cutting line may be spaced apart from the first side edge a distance of 20-80% of the width of the compound base web.

Cutting the compound base web along a machine direction centre line through the base web and the continuous elastic waistband component produces two panel webs of equal width in the cross machine direction. It may be preferred to arrange the cutting line offset from the base web centre line, in order to produce a pant article having differently sized front and rear panels.

If the waistband component is placed symmetrically along the cutting line, the waistband portions will be of equal width and a pant article produced from the chassis web will have an elastic waistband of uniform configuration encircling the waist opening of the article. A pant article having front and rear waist elastic of different width may be produced by placing the attachment area and thereby the waistband component with unequal parts of the waistband component on each side of the cutting line.

By way of example only, it may be desirable to produce a pant article having a larger rear portion than front portion and/or having a broader elastic waistband at the rear than at the front of the pant article.

As disclosed herein, the compound base web is preferably an elastic base web or a web which may be rendered elastic by activation. Activation methods include mechanical activation such as incremental stretching and activation by heat treatment. The compound elastic base web may comprise elastic and non-elastic components and layers and may comprise at least one non-elastic layer and at least one elastic layer. The at least one non-elastic layer may be a nonwoven material and may be coextensive with the elastic layer or may have an extension in the cross machine direction which is different from the extension of the elastic layer in the cross machine direction. The elastic layer may be a layer of multiple elongated elastic elements such as threads, strings or bands arranged parallel to each other, an elastic scrim, an elastic nonwoven web, an elastic film, etc. The compound elastic base web is elastic at least in the machine direction, but may be elastic also in other directions such as in the cross machine direction. As set out herein, the base web may be provided as an initially inelastic web which is subsequently rendered elastic by activation to make the base web elastically stretchable at least in the machine direction.

As disclosed herein, the compound elastic base web may comprise an elastic film. The elastic film layer preferably extends in the cross machine direction CD over the full width of the compound base web. The elastic film is preferably a breathable film.

An elastic film as a means for providing elastification may be preferred over laminates which have been elastified with threads as it provides a more even elastification and a generally smoother elastic panel than laminates which are elastified by elastic threads. An elastic film may be elastically stretchable in more than one direction, such as bi-axially stretchable and may provide the compound base web with bi-directional elasticity or multi-directional elasticity.

As set out herein the waistband component may be elastic or non-elastic. An elastic waistband component may comprise threads, film, bands, foam, etc. as known in the art. A non-elastic waistband component may be used to provide a disposable pant article with a tailored hem at the waist edge. A tailored hem at the waist edge provides a disposable pant article with an enhanced likeness to ordinary underwear and may improve user comfort and fit of the article by counteracting roll-over of the waist-line. However, the non-elastic waistband is preferably arranged to be rendered elastic by activation, as set out herein. The waistband component may comprise or consist of materials having any desired colour.

The waistband component is applied as a pre-fabricated elastic or elastified band-shaped component comprising one or more carrier webs. A carrier web may be an elastic or non-elastic web, such as an elastic or non-elastic nonwoven material, an elastic or non-elastic film or a combination of different materials.

The waistband component may have a width in the cross machine direction of from 10 mm to 200 mm, such as from 10 mm to 100 mm, or from 10 mm to 80 mm. In a finished pant article, the waistband may have a width of from 5 mm to 100 mm, such as from 5 mm to 50 mm, or from 5 mm to 40 mm.

The first and/or the second continuous base web may comprise or consists of a bi-laminate web comprising a nonwoven layer and an elastic layer.

A compound elastic base web in the method as disclosed herein may comprise or consists of a tri-laminate web comprising two outer nonwoven layers and an intermediate elastic layer between the outer nonwoven layers. A three-layer compound elastic base web may be formed by one of the first and second continuous base webs being a laminate of a nonwoven layer and an elastic film layer and the other of the first and second continuous base webs being a nonwoven layer which is laminated to the film side of the bi-laminate base web. The nonwoven base web may be bonded to the bi-laminate base web by stretch bonding, i.e. while the elastic bi-laminate web is held in a stretched state, such as stretched by 50-600% in the machine direction MD, to retain the elastic properties of the elastic film layer in the compound base web.

A compound elastic base web comprising an elastic film layer laminated between two nonwoven layers may alternatively be produced by laminating an elastic film as a separate layer between the first continuous base web and the second continuous base web before or after attaching the continuous waistband component to the first continuous base web and before attaching the second continuous base web to the first continuous base web.

A three-layer nonwoven-film-nonwoven laminate provides elastic panels with smooth, soft and skin-friendly textile surfaces. The laminate may be produced by any known method or combination of methods such as stretch-bonding methods, methods involving incremental stretching, etc.

It may be preferred that an elastic waistband component comprises multiple elongate elastic elements, such as elastic threads, bands, strings, etc.

The elastic waistband web may be attached to the continuous base web by stretch-bonding, i.e. by bonding the waistband component to the continuous base web while one or both of the waistband component and the continuous base web is stretched at least in the machine direction.

The waistband component may be attached to the first continuous web using any known bonding method or combination of bonding methods such as ultrasonic bonding, adhesive bonding, stitch-bonding, thermo-bonding, etc.

Likewise, the first and second continuous base webs may be attached to each other using any known bonding method or combination of bonding methods such as ultrasonic bonding, adhesive bonding, stitch-bonding, thermo-bonding, etc.

When the first continuous base web is an elastic base web, and the waistband component is an elastic waistband component, the elastic waistband component and the continuous first elastic base web may be held stretched from 50% to 600% in the machine direction when attaching the waistband component to the continuous elastic first base web.

The elastic waistband component may be stretched to the same or to a different degree than the continuous first elastic base web. The end elasticity depends on the materials used, such that even if the elastic base web and the elastic waistband component are stretched to the same degree during the attachment step, the panel web may have a higher elastic tension in the waistband portion than in a portion of the panel web constituted only by the base web material as a result of permanent deformation of the base web caused by the stretching.

As disclosed herein, the first panel web and the second panel web which are formed by the severing step may be shifted into a position wherein the first side edge and the second side edge are arranged at a distance from each other with a gap between the first panel web and the second panel web. In the connecting step the first side edge is indirectly connected to the second side edge by means of a bridging member. The bridging member has an extension in the cross machine direction which is greater than the gap and the bridging member is applied across the gap and is bonded to the first panel web and to the second panel web. The bridging member may have any suitable extension in the cross machine direction from a minimum extension which is only slightly greater than the gap between the panel webs such that only an edge portion of the bridging member overlaps with each of the panel webs up to an extension where the bridging member extends all the way to the cut edges of both panel webs.

The bridging member may comprise a continuous bridging web, i.e. a bridging web which is continuous in the machine direction. As set out above, the continuous bridging web may be attached to the first and second panel webs only along the first and second side edges of the panel webs, or may be attached in an overlapping configuration with all or part of one or both of the panel webs. If a non-elastic continuous bridging web is attached to an elastic panel web in an overlapping configuration, the elastic panel web may be stretched in the machine direction during bonding with the bridging web to retain the elastic properties in the parts of the bridging web which overlap with the elastic panel webs. Bonding of a continuous bridging web may be made using any bonding method, as known in the art, such as adhesive bonding, thermowelding, ultrasonic bonding, etc.

As an alternative to a continuous bridging web, the first panel web and the second panel web may be connected by multiple discrete bridging members which are applied intermittently in the machine direction and which are arranged in the cross machine direction to bridge the gap between the first panel web and the second panel web. The discrete bridging members may comprise or consist of absorbent material. The absorbent material may be applied in the form of absorbent fibrous materials, absorbent films, absorbent foams, absorbent particulate material, etc. and may be incorporated in an absorbent core.

The method as disclosed herein may further involve intermittently applying absorbent cores to the coherent chassis web. The absorbent cores are arranged with a longitudinal direction of the absorbent cores coinciding with the cross machine direction and are spaced apart in the machine direction. The absorbent cores may be placed on the chassis web after the first and the second panel webs have been connected either directly or indirectly by means of a bridging member. Alternatively, the absorbent cores may be part of or may constitute individual bridging members and may be used to indirectly connect the first panel web with the second panel web to form the coherent chassis web. The absorbent cores may be part of a core pack, as disclosed herein.

When one of the first and second continuous base webs is an elastic base web and, the elastic waistband component may be cut off from a side portion of the elastic base web before attaching the waistband component to the first elastic base web to create a waistband area on the first elastic base web having different elastic properties from the remainder of the first elastic base web.

If the same elastic material is used for a continuous base web as for the elastic waistband component, additional elastic elements may be attached along the side edge of the elastic web before cutting off the waistband strip. Such additional elastic elements may be used to modify the elastic properties of the base web in the cut-off portion, e.g. to increase the elastic tension in the base web within the area which is to be used as a waistband component.

The severing step may be performed by cutting along a non-linear cutting line.

A set out herein, directly after the severing step, the cut edge contour of the first panel web is in complete register with the cut edge contour of the second panel web. In other words, the contour of the cut edge on the first panel web is the mirror image of the contour of the cut edge on the second panel web. After the shifting step, the first and second panel webs may have been shifted not only in the cross machine direction but also in the machine direction such that the non-linear cut edges of the panel webs may have been moved out of register with each other.

A non-linear cut edge may be useful for providing a pant article with a softer, less distinct edge. Accordingly, a non-linear waistband edge may counter-act chafing and red-marking of the skin at the waist of a wearer. A non-linear cut edge may also be useful to provide a pant-article with a more tailored and visually appealing appearance mimicking the appearance of regular underwear having a decorative band at the waist opening edge. As set out herein, it is an aim to provide a manufacturing method for disposable pant articles which allows simple and efficient mass-production of disposable pant articles which are more under-wear like and less like diapers or diaper pants than previously offered disposable pant articles.

The non-linear cutting line may have an undulating shape, such as a sinusoidal shape or a zig-zag shape. It may be preferred that the non-linear cutting line has a shape which is symmetrical about a centreline extending through the cutting line in the machine direction, as this will produce cut waist edges having the same appearance at a front waist edge and a rear waist edge of a pant article produced from the chassis web.

The method as disclosed herein may further comprise arranging leg elastic on one or more of the first and second continuous base webs, the compound base web and the coherent chassis web. In addition or as an alternative thereto, a core pack may comprise leg elastic. Furthermore, leg elastic may be provided on any type of bridging member such as on a bridging web or on a discrete bridging member such as a core pack.

As disclosed herein, leg openings may be intermittently arranged in the coherent chassis web.

The leg openings may be formed completely in a bridging web or partially in a bridging web and partially in one or both of the first and second panel webs.

When the first and second panel webs are connected by discreet bridging members, side edges of the bridging members together with portions of the side edges of the first and second panel webs may form the leg openings without any additional shaping of the leg openings being required. If using discrete bridging members to connect the side edges of the first and second panel webs, the side edges of the bridging members may be provided with a leg curvature before being attached to the first and second panel webs. Alternatively, a shaped leg edge may be formed in a leg opening shaping step after attaching the bridging members to the first and second panel webs. A shaped leg edge may be formed by cutting off edge parts of the bridging members and/or by cutting off edge parts of the first and/or second panel webs.

The coherent chassis web may be provided with alternating crotch portions and leg opening portions arranged centrally along the chassis web in the machine direction by connecting the first and second panel intermittently either directly or by applying discrete bridging members between the inwardly facing side edges of the first and second panel webs. The leg opening portions may subsequently be shaped to provide a desired curvature to the leg opening edge. Another way of forming alternating crotch portions and leg opening portions in a coherent chassis web is by cutting out leg openings in a chassis web which has been formed by continuous connection of the inwardly facing side edges of the first and second panel webs. The side edges of the first and second panel webs may be either be directly connected with each other or may be indirectly connected by means of a bridging web.

As set out herein, the bridging members may each comprise or consist of a core pack, the core pack comprises at least an absorbent core and a backsheet, such as a liquid impermeable or at least liquid resistant backsheet. The core pack may optionally comprise additional components such as a liquid permeable topsheet, elastic elements, liquid acquisition components etc. as known in the art.

The method as disclosed herein may further comprise the step of folding the coherent chassis web along a folding line extending in the machine direction, the folding step being carried out before or after arranging leg openings in the coherent chassis web.

Folding is preferably made centrally in the chassis web to create pant articles having front and rear portions of equal height although it is conceivable to fold along a fold line being off-set from a machine direction centre line through the coherent chassis web. An off-set fold line may be used e.g. to produce an article having a lower front waist line than rear waist line.

The method as disclosed herein may further comprise the step of forming side seams between the first and second panel webs at hip portions of the coherent chassis web, the side seams extending in the cross machine direction and delimiting individual pant article blanks in the machine direction.

Side seams may be provided in any manner as known in the art such as by ultrasonic welding, thermobonding or by adhesive or mechanical connections or by any combination of connection methods. Adhesively formed side seams or side seams comprising mechanical fasteners such as hook-and-loop fasteners or adhesive fasteners such as reclosable tapes, are applied to the panel webs before folding of the chassis web. Leg openings may have been formed before folding of the chassis web and forming of the side seams, or may be formed after folding the web or after folding the web and after forming the side seams.

The method as disclosed herein may further comprise a step of forming individual pant articles by cutting the coherent chassis web in the cross machine direction at the side seams.

Disclosed herein is also a disposable pant article having a waist opening with a waist opening edge, the pant article comprising a front panel and a rear panel, the front panel comprising a front panel material having a front panel material edge and a front waistband having a front waistband edge, the front waistband being attached at a front waist edge portion of the front panel material between first and second layers of the front panel material, the rear panel comprising a rear panel material having a rear panel material edge and a rear waistband having a rear waistband edge, the rear waistband being attached at a rear waist edge portion of the rear panel material between first and second layers of the rear panel material. The waist opening edge is a cut edge and comprises a front waist opening edge portion and a rear waist opening edge portion, the front waist opening edge portion comprising the front panel material edge and the front waistband edge and the rear waist opening edge portion comprising the rear panel material edge and the rear waistband edge.

The front and rear panels of the disposable pant article may comprise or consist of a first elastic material, and the front waist band and the rear waist band may comprise or consist of a second elastic material. Thereby, the disposable pant article is provided with an elastic waist zone at the waist opening edge which elastic waist zone comprises both the first elastic material and the second elastic material. The elastic waist zone has a width which is determined by the width of the waistband. The width of the waistband or the elastic waist zone is the extension of the waistband or the waist zone perpendicular to the waist opening edge corresponding to the cross machine direction during production of the disposable pant article. The width of the waistband may be from 5 mm to 100 mm, such as from 5 mm to 50 mm, or from 5 mm to 40 mm.

As set out herein, the first and second elastic material may be the same or different materials and may be separately selected to provide the waist zone with suitable elastic properties.

The cut waist opening edge may be a non-linear cut edge, as set out herein.

The disposable pant article may be an absorbent pant article and may comprise an absorbent core. The absorbent core may be part of a core pack, as set out herein.

The pant article as disclosed herein may be produced from a coherent chassis web by further processing of the chassis web as set out herein and may comprise leg elastic, fasteners, etc. as known in the art.

The compound base web to which the waistband component is attached forms a front and a rear panel of a pant article as disclosed herein each front and rear panel having a corresponding front and rear elastic waistband formed from a part of the waistband component. After the front and rear panels have been connected at the side seams, the front and rear waistbands form a continuous waist encircling waistband. The processes disclosed herein make it possible to produce a pant article having two layers of elastic material in the waistband area of the article. The elastic materials in the two layers may be the same type of elastic material or may be different, as set out herein. Accordingly, the elastic materials may differ in one or more respects with regard to the elastic properties, the material composition, the physical form of the elastic material, etc.

Although elastic waistbands are generally preferred, the waistband component may be elastic or non-elastic, as set out herein.

An elastic laminate web which may be used for forming the panel portions of the chassis webs as disclosed herein is composed of at least one layer of fibrous nonwoven material and an elastic layer. The nonwoven layer is chosen so that it provides a soft and cloth-like feel and appearance to the laminate. Examples of suitable materials are meltblown webs, spunbond materials, bonded, carded webs, spunlaced webs, and creped nonwovens. Any soft, flexible and optionally extensible nonwoven materials and nonwoven laminates may be used.

The basis weight of a nonwoven web used in the elastic laminate is suitably from 6-80 $g/m^2$ and preferably from 13-50 $g/m^2$. Examples of suitable polymers used in the nonwoven web are polyethylene, polyesters, polypropylene and other polyolefin homopolymers and copolymers. Natural fibres, for example cotton, may also be used as long as they provide the desired properties. A mixture of polymers can contribute to a higher flexibility of the nonwoven layer, and thereby give the nonwoven material a higher elongation at maximum load. A mixture of polyethylene and polypropylene polymers has proven to provide good results in this respect. However, nonwovens having other fibre mixtures may also be used.

The elastic layer may be an apertured or non-apertured elastic film, an apertured film providing enhanced breathability. The elastic layer may have a basis weight of between and 120 $g/m^2$, preferably between 15 and 60 $g/m^2$. The elastic layer may be of any suitable elastic polymer, natural or synthetic. Some examples of useful materials for the elastic layer are low crystallinity polyethylenes, metallocene-catalyzed low crystallinity polyethylenes, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable elastic film is an apertured three-layer elastomeric film with the composition polyethylene-styrene/ethylene/butadiene/styrene-polyethylene (PE-SEBS-PE).

As the elastic film will extend over all or at least a major portion of the front and back panels of a pant article produced from a base web comprising an elastic film, it is highly preferred that the elastic film is a breathable film, such as a porous breathable film and/or an apertured breathable film, as set out herein.

An elastic laminate can be produced with any useful method such as by stretch-bonding, or may be an incrementally stretched elastic laminate produced according to the methods disclosed in WO 03/047488. The laminates produced in WO 03/047488 are three-layer laminates comprising an elastic film sandwiched between two layers of non-elastic nonwoven. In order to render the laminate elastically stretchable, it is subjected to an activation treatment. The activated laminate is produced by incrementally stretching the elastic film layer between two non-elastic cloth-like layers. Incremental stretching is carried out by passing the laminate between intermeshing gear rollers. The non-elastic cloth-like layers are fully or partially broken or torn during the activation process so that the elasticity of the laminate after activation is mainly determined by the elasticity of the elastic film layer. It is also conceivable to first produce a two-layer incrementally stretched elastic laminate which is further processed by stretchbonding the film-side of the activated elastic bi-laminate to a second nonwoven layer.

The nonwoven web and the film may be extrusion bonded or may be bonded by adhesive. The laminate may be incrementally stretched to activate the elasticity of the film layer.

Incremental stretching can be made to a point below the elongation at peak load of the nonwoven web to retain some strength in the nonwoven web. Alternatively, the stretching may be carried out so that the nonwoven is completely torn, as disclosed in WO 03/047488.

By selecting nonwoven materials having thermoplastic properties for the elastic laminate webs used for producing the panel webs disclosed herein, the panel webs can be seamed to other components by thermo-bonding and ultrasonic welding techniques. For example, it may be beneficial if at least one nonwoven web is substantially or completely made of thermoplastic fibres, such as polypropylene fibres. The nonwoven layer or layers can then be used to form side seams with good tensile strength. Since thermo-bonds used in side seams usually penetrate the welded materials, the orientation of the laminate with respect to the nonwoven layers is normally not crucial for obtaining a thermobonded seam as long as at least one of the layers is predominantly made of thermoplastic fibres or the combination of the two layers contain sufficient thermoplastic material in order to achieve sufficient bond strength. The side seams are preferably breakable side seams, i.e. welds that may be peeled or torn apart when the pant article is removed.

Definitions

An absorbent pant article as used herein is an absorbent garment that is configured to fit a wearer as a pair of underpants, implying that the absorbent article comprises side seams at the waist-encircling portion of each article and that the article has a waist opening and two leg openings. Usually the side seams are formed in the chassis structure of the article after any other production steps have been performed such as after the application of one or more features such as leg elastic, waist elastic, inner raised barriers, size tags, absorbent components, topsheet layers, barrier layers, reinforcements, patches, etc. Side seams may be formed in any suitable manner such as adhesively, or by heat or ultrasonic welding. The side seams are preferably made to be openable side seams implying that the side seams are strong enough to withstand the pulling and stretching forces applied to the side seams when putting on and wearing the pant article but may be broken without undue tearing of the article when the article is being removed from the wearer. Openable side seams may be peelable side seams or may have been made openable by arranging tear strips, perforations, or other types of weakenings along the side seams. The openable side seams may be reclosable to allow inspection, as known in the art. The side seams are preferably designed so that they can withstand the tensile forces which arise when the article is being put on and is being worn, but such that they can be torn apart or opened in a controlled manner when the pants are taken off or to check if an absorbent pant-type article needs changing.

A pant-type article having openable side seams may be provided with fasteners in order to provide reclosability of the side seams. The fasteners may be mating fasteners commonly used in the art and well known to the person skilled in the art such as hook-and-loop fasteners, adhesive fasteners mating with a landing member, press-studs, etc. The mating fasteners are preferably reclosable fasteners so that the article can be repeatedly opened and reclosed for inspection and for readjustment of the fit.

In this context, an elastic material is defined as a material having a permanent elongation after relaxation of less than 10% after the material has been subjected to an elongation of 30% in the elasticity test specified hereinafter.

A non-elastic material is a material that does not fall within the definition of an elastic material. Accordingly, a non-elastic material as used herein is a material that may be stretchable or non-stretchable. In the case of a stretchable material, the material has a permanent elongation after stretching and relaxation of more than 10% after having been subjected to an elongation of 30% as determined according to the elasticity test.

An elastic waistband component may be supplied as an elastic band, of any suitable kind, such as an elastic laminate, an elastic foam strip, an elastic nonwoven, as a non-elastic material which has been elasticized with elastic threads or strings, bands, elastic scrim, etc. An elastic waistband component may be made by attaching elastic elements such as threads, bands or strings in a pre-tensioned state between two layers of nonwoven non-elastic material. A waistband component may be formed from two separate layers of nonwoven material or may be made from a single layer of nonwoven material that is folded into a two-layer structure. Alternatively, it is possible to use the same elastic web material as is used to form the panel portions of the panel webs as disclosed herein to create the elastic waistband web. Any commonly used elastic material such as natural or synthetic rubber, elastic foam, etc. can be employed.

A "core pack", as used herein is a component in an absorbent pant article which comprises an absorbent core provided with a backsheet. The backsheet is preferably a liquid barrier layer which is liquid impermeable or at least resistant to liquid penetration. The core pack may also comprise a liquid permeable topsheet and the absorbent core may be enclosed between the topsheet and the backsheet. The absorbent core may comprise any type of absorbent material such as cellulose fluff pulp, superabsorbent material, etc. as known in the art as well as non-absorbent components such as non-absorbent fibres, binders, shaping elements, fluid distribution elements, etc. The core may have any suitable construction with different materials and/or different properties in different layers and/or in different zones, as known in the art and may be generally flat or may have a three-dimensional profile. The core pack may have any suitable planar shape such as rectangular, hourglass-shaped trapezoid shape, etc. For manufacturing reasons, a rectangular shape may be preferred.

The core pack may further comprise elastic elements, such as leg elastic elements which may be arranged along the side edges of the core pack.

The term "panel" is used herein to denote a functional part of a pant article chassis while the terms "region" and "portion" are used to denote the location of a particular feature of the article in the chassis or to describe the intended positioning of a particular part of the article in relation to a user's body. A region or portion may have an extension fully or partially covering one or more panels.

When components are joined, attached or secured to each other they are separate parts which have been bonded by any suitable means such as adhesively, by stitching or by ultrasonic welding or thermo-welding. The term joined also includes separable (openable) seams, such as separable side seams and reclosable side seams such as hook-and loop side seams, reclosable tape seams, snap fasteners, etc. Components which are arranged on each other need not be bonded, although as used herein, the term "arranged" should be broadly understood to also include bonded components.

A web of material as used herein is any generally two-dimensional, flexible material or combination of materials such as plastic films, nonwovens, foams or textiles. The web may be a multicomponent web comprising several layers and/or areas of different materials. A web as used herein may be in the form of a continuous web or in the form of a discreet web.

A chassis web as used herein is a continuous web comprising multiple assembled components. The chassis web may be further processed and converted into individual pant articles. The chassis web may be cut to form shaped leg openings. The web may be folded and side joins may be formed in the folded web between individual chassis blanks wherein each chassis blank optionally carries an integrated core component, e.g. in the form of a core pack. Individual pant articles may be separated from the chassis web by cutting the web at side seams. The cutting step may be performed by cutting between two parallel bond lines forming the side seams and being arranged at a small distance from each other in the machine direction MD of the chassis web. The side seams may alternatively be formed as one single broad bond line which is cut in two in the cutting step. Further ways of forming side seams in a pant-type absorbent article is disclosed in WO 2007/138373 and WO 2008/079061.

A laminate as used herein is a material web comprising at least two different and distinct layers having overlapping parts, the overlapping parts being joined to form the laminate.

BRIEF DESCRIPTION OF THE DRAWINGS

The present invention will be further explained hereinafter by means of non-limiting examples and with reference to the appended drawings wherein:

FIG. 2 shows a pant article produced according to the methods as disclosed herein; and FIG. 3 shows a cross-section along the line III-III through a waist edge portion of the pant article in FIG. 2.

DETAILED DESCRIPTION

It is to be understood that the drawings are schematic and that individual components, such as layers of material are not necessarily drawn to scale. The pant diaper shown in the figures is provided as an example only and should not be considered limiting to the invention. The production method and the waistband construction disclosed herein are applicable to any type of disposable absorbent and non-absorbent pant article such as disposable hygienic pants, pant diapers, menstrual panties, incontinent pants, etc. Accordingly, the scope of the invention is determined solely by the appended claims.

Figure 1A:
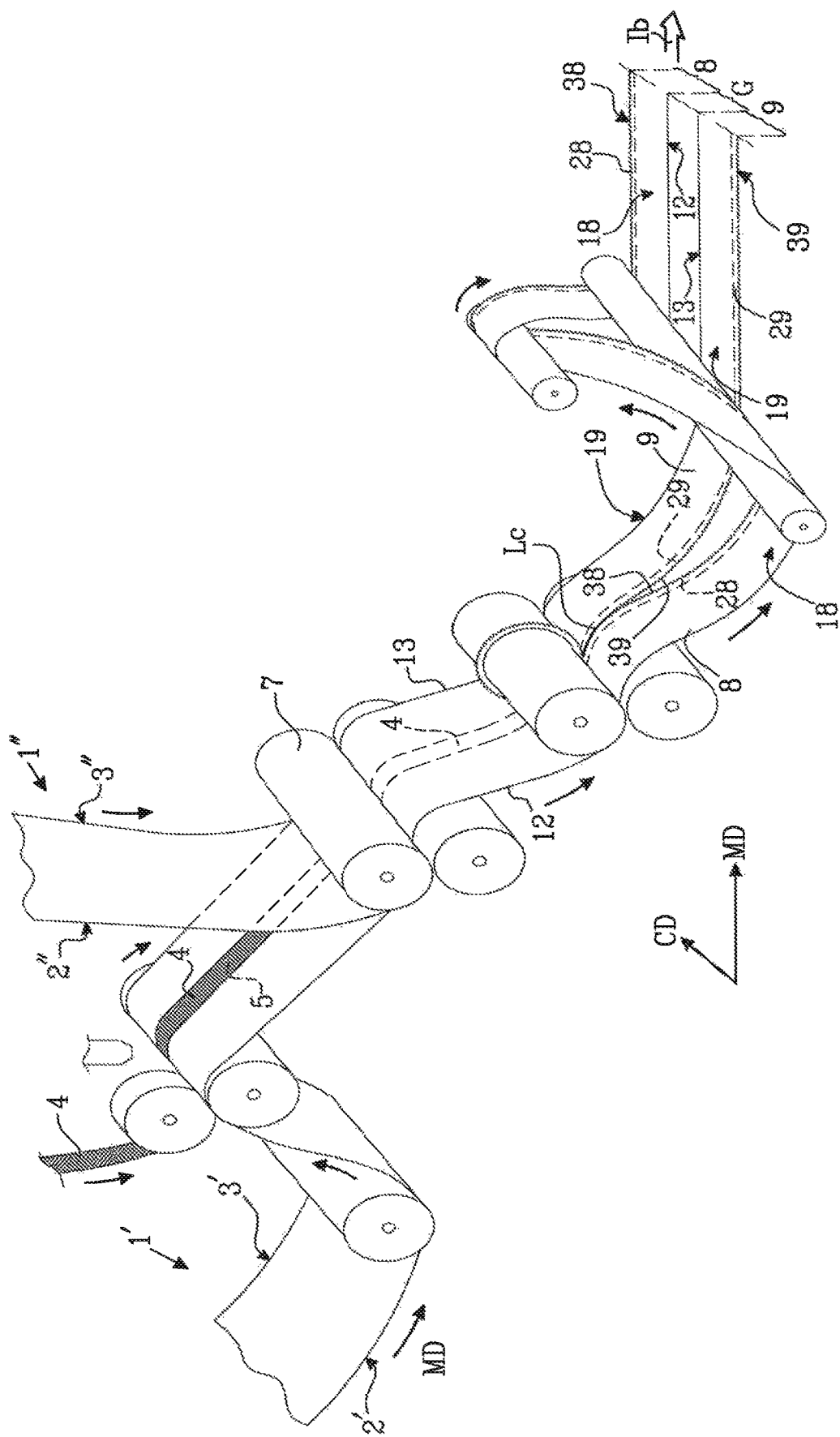
FIG. 1a shows schematically a first part of a method for producing a pant article.
Figure 1B:
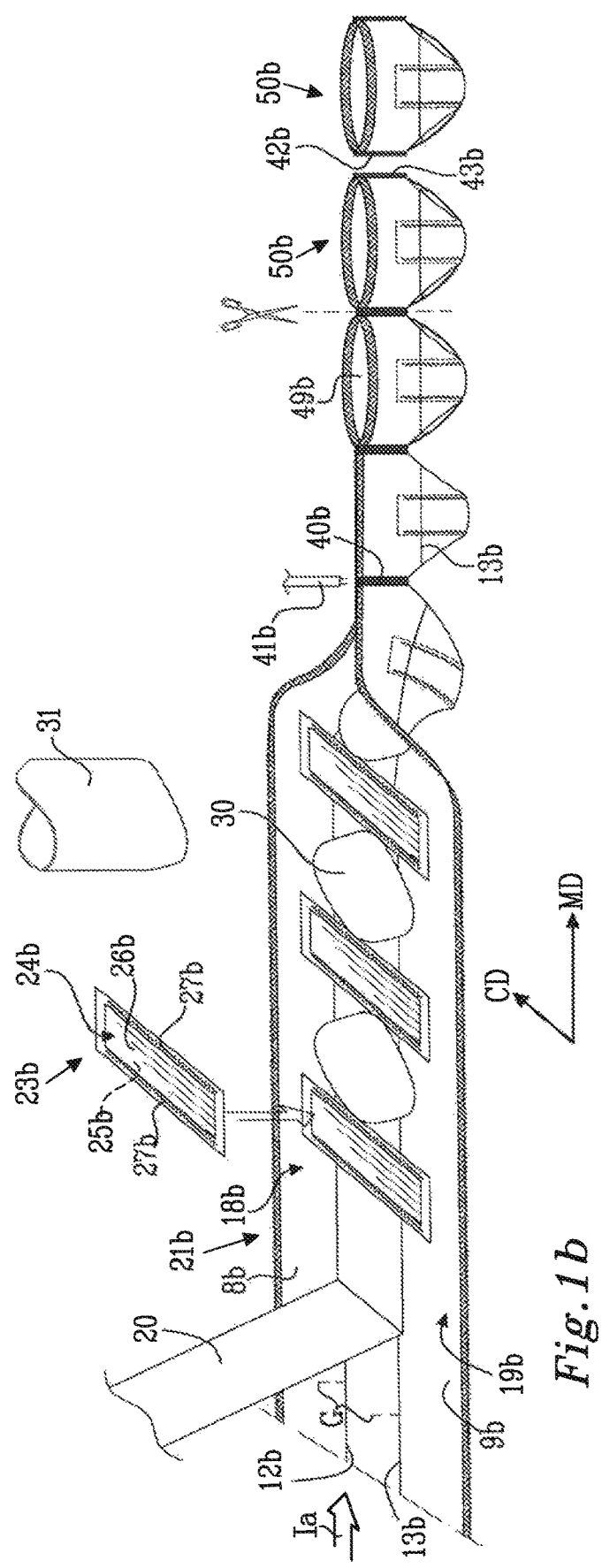
FIG. 1b shows schematically a first embodiment of a second part of a method for producing a pant article.
Figure 1C:
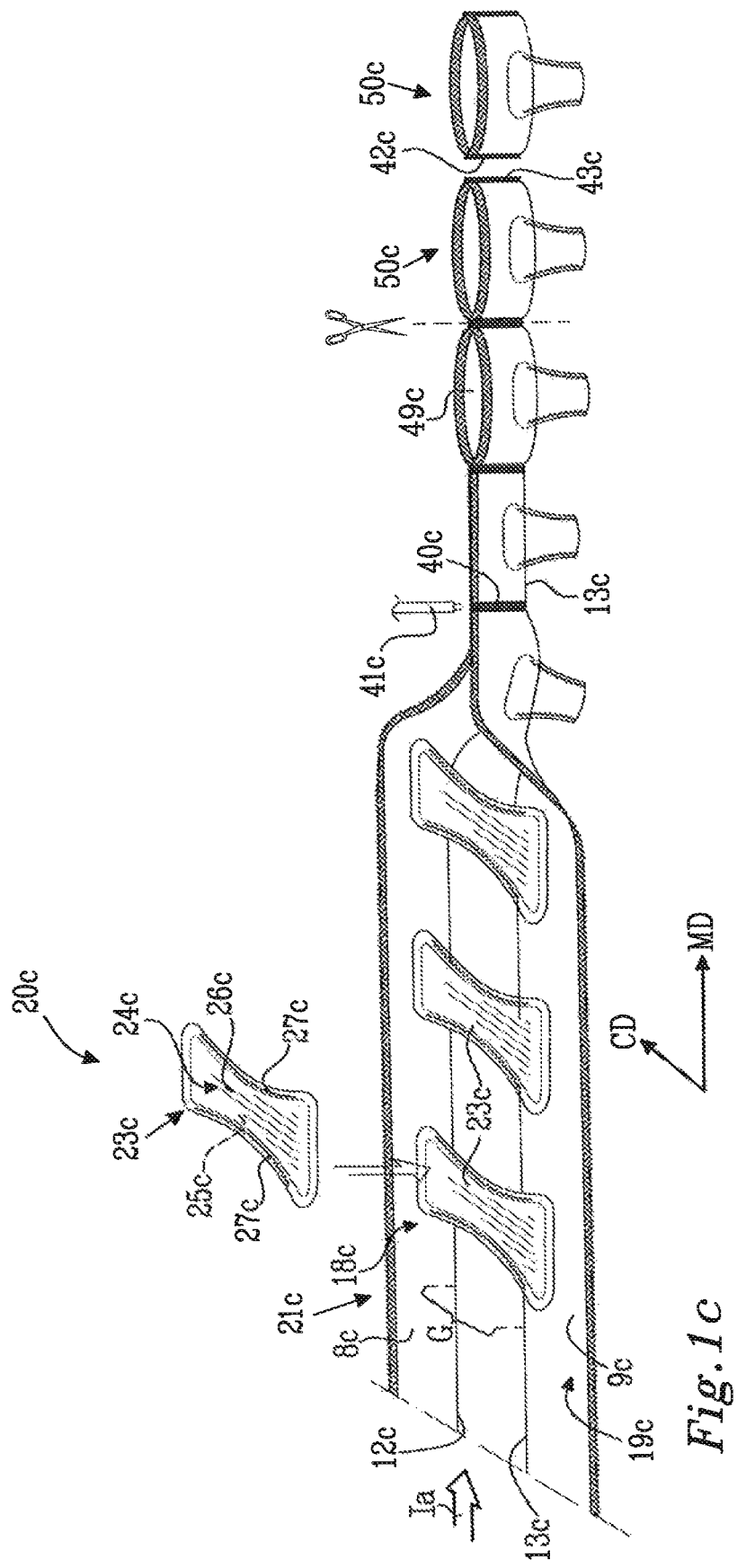
FIG. 1c shows schematically a second embodiment of a second part of a method for producing a pant article.

With reference to FIGS. 1a, 1b, and 1c, two partly different methods for producing pant articles are illustrated. The methods are intended as examples only, and it is to be understood that a chassis web produced from the methods as disclosed herein may be used in the production of disposable pant articles of different designs, such as non-absorbent pant articles, pant articles having leg elastic elements arranged along part or all of the leg openings, pant articles having different side seam arrangements from those shown herein, such as side seam arrangements including fastener elements, etc.

As is shown in FIG. 1a, a continuous first base web 1' is fed in a machine direction MD. The continuous base web 1' has first and second parallel side edges 2',3' extending in the machine direction MD. A continuous waistband component 4 is attached to the first base web 1' in an attachment area 5. The attachment area 5 extends in the machine direction MD and is arranged between the first and the second side edges 2',3' of the first continuous base web 1'. The attachment area 5 and thereby also the waistband component 4 are spaced apart from at least one of the first and the second side edges, 2,3. In the example shown in FIG. 1a, the attachment area 5 is a band-shaped area corresponding to the shape of the band-shaped waistband component, which area is spaced apart an equal distance from each of the side edges 2',3' of the first base web 1' implying that the attachment area 5 is centrally arranged on the first continuous base web 1' in the machine direction MD. Alternatively, the attachment area 5 may be arranged set off towards one of the side edges 2', 3'.

A second continuous base web 1" having first and second side edges 2", 3" extending in the machine direction MD is fed in the machine direction MD and is attached to the first continuous base web 1' and to the continuous waistband component 4. The second continuous base web 1" is arranged to cover at least the continuous waistband component 4. In the example shown in FIG. 1a, the second continuous base web 1" is coextensive with the first continuous base web 1'. The joined first and second continuous base webs 1', 1" form a compound base web 11 having first and second side edges 12, 13, the attachment area 5 being spaced apart from at least one of the first and the second side edges 12,13 of the compound base web 11.

It may be preferred that the first and/or the second continuous base web 1', 1" is an elastic base web and that the first and second continuous base webs 1', 1" are joined to each other so that the assembled compound base web 11 is also an elastic base web. The compound elastic base web may comprise elastic and non-elastic components and layers and may be a laminate structure comprising at least one non-elastic layer and at least one elastic layer. The elastic layer may be a layer of multiple elongated elastic elements such as threads, strings or bands arranged parallel to each other, an elastic scrim, an elastic nonwoven web, an elastic film, etc. It may generally be preferred that the continuous base web 1 comprises an elastic film layer, such as a breathable elastic film layer, as set out herein. An elastic base web is elastic at least in the machine direction, over the full width thereof, but may be elastic also in other directions such as in the cross machine direction.

As set out herein the waistband component may comprise threads, film, bands, foam, etc. as known in the art. The waistband component is applied as a pre-fabricated non-elastic, elastic or elasticated waistband component comprising one or more carrier webs. A carrier web may be an elastic or non-elastic web, such as an elastic or non-elastic nonwoven material, an elastic or non-elastic film or a combination of different materials. It may be preferred that a carrier material which will be placed in direct skin contact when the disposable absorbent pant article is worn be made of a textile or textile-like material, such as a nonwoven material.

An elastic waistband component 4 may be attached to an elastic first continuous base web 1' while both the waistband component 4 and the first continuous base web 1' are being stretched in the machine direction MD. An elastic waistband component 4 may alternatively be stretch-bonded to a non-elastic first continuous base web 1'.

The elastic waistband component 4 and a continuous first elastic base web 1' may be held stretched from 50% to 600% in the machine direction when attaching the elastic waistband component to the continuous elastic base web.

The elastic waistband component 4 may be stretched to the same or to a different degree from the first continuous elastic base web 1'. The end elasticity depends on the materials used, such that even if an elastic base web and the elastic waistband component are stretched to the same degree during the attachment step, the resulting panel web may have a higher elastic tension in the waistband portion than in a portion of the panel web constituted only by the base web material as a result of permanent deformation of the base web caused by the stretching.

The waistband component 4 may be attached to the first continuous base web 1' using any known bonding method or combination of bonding methods such as ultrasonic bonding, adhesive bonding, stitch-bonding, thermo-bonding, etc. In FIG. 1a, the bonding is exemplified by ultrasonic bonding in a bonding unit 6.

Subsequent to attaching the waistband component 4 to the first continuous base web 1' within the attachment area 5, and joining the second continuous base web 1' with the first continuous base web 1', the compound base web 11 and the attached elastic waistband component 4 are severed by cutting along a cutting line $L_C$ extending through the attachment area 5 in the machine direction MD thereby creating a first panel web 8 having a first side edge 12 and comprising a first panel portion 18 and a first waistband portion 28 and a second panel web 9 having a second side edge 13 and comprising a second panel portion 19 and a second waistband portion 29. The first panel web 8 and the second panel web 9 extend in the machine direction MD with the first and second waistband portions 28, 29 and first and second cut edges 38, 39 facing each other in a side-by-side arrangement.

In the process shown in FIG. 1a, the severing step is performed using a cutting roller 7, However, it should be understood that any alternative cutting method may be used such as laser cutting, etc.

The positions of the first panel web 8 and the second panel web 9 are then shifted in a cross machine direction CD perpendicular to the machine direction MD. Thereby, the first and the second panel webs 8, 9 are brought into a new parallel arrangement with the first and second cut edges 38, 39 facing away from each other in the cross machine direction CD and with the first and second side edges 12, 13 of the first and second panel webs 8, 9 facing each other in the cross machine direction CD.

Cutting the compound base web 11 with the continuous elastic waistband component 4 centrally as shown in FIG. 1a produces two panel webs 8, 9 of equal width in the cross machine direction CD. As set out herein, it may be preferred to arrange the cutting line $L_C$ offset from the base web centre line, in order to produce a pant article having front and rear panels of different sizes. The compound base web 11 has a width W between the first and the second side edges 12, 13 and the cutting line $L_C$ may be placed spaced apart from the first side edge 12 a distance of 20-80% of the width W of the compound base web 11.

As set out herein, depending on the desired end-design of the pant-articles produced with the methods as disclosed herein the attachment area 5 and the elastic waistband component 4 may be arranged offset from the centre of the compound base web 11 towards one of the side edges 12, 13 such that the waistband component 4 is asymmetrically placed on the compound base web 11. Such arrangement may be preferred when producing a pant article having differently sized front and rear panels. The elastic waistband component 4 may even be attached along one of the side edges of the compound base web 11 with a side edge of the waistband component coinciding with a side edge of the compound base web.

In the embodiment shown in FIG. 1a, the waistband component 4 is placed symmetrically along the cutting line $L_C$, producing waistband portions 28, 29 of equal width. A pant article having front and rear waist elastic of different width may be produced by placing the attachment area 5 and thereby the waistband component 4 with unequal parts of the waistband component 4 on each side of the cutting line $L_C$.

In an embodiment (not shown) where the waistband component 4 is placed along one of the side edges of the compound base web 11, severing the compound base web produces a first panel web having the panel portion and the waistband portion arranged in a completely overlapping configuration while the second panel web has a waistband portion which overlaps with only an edge part of the panel portion. The first panel web is a narrow band-shaped full-width laminate of one or both of the first and second base webs 1', 1" and the waistband component 4. The band-shaped first panel web may be shifted and attached as a waistband along the side edge 13 of the second panel 9 web which is opposite to the edge part at the cut edge 39 of the second panel web which edge part overlaps with the waistband portion of the second panel web 9.

In the illustrated example, severing of the compound base web 11 is made along a non-linear cutting line $L_C$, exemplified by a zig-zag shaped cutting line. Alternatively, the cutting line $L_C$ may be linear, or may have any other suitable shape such as a sinusoidal curve shape. It may be preferred that the cutting line has a symmetrical curve shape as a symmetrical cutting line produces cut edges having the same general shape and appearance. A pant article produced from a web which has been severed along a symmetrical cutting line will have a uniformly shaped waist edge, i.e. a waist edge having the same appearance on the front of the article as on the rear of the article.

As illustrated in FIG. 1a, after the shifting step, the first and second panel webs 8, 9 extend parallel to each other and are arranged at a distance from each other in the cross machine direction CD with a gap G between the inwardly facing side edges 12, 13. In other embodiments, as set out herein, the first and second panel webs 8, 9 may be shifted into a position where the inwardly facing side edges 12, 13 are in direct contact with each other such that the first and second panel webs 8, 9 can be directly connected with each other along the inwardly facing side edges 12, 13 and thereafter further processed and converted into individual pant articles.

FIG. 1b is a highly schematic representation of a method for converting the elasticated, severed and shifted web parts produced by the steps shown in FIG. 1a into individual pant articles. The method involves forming a chassis structure carrying an absorbent core component. The core component may be incorporated into the process of forming a pant article as a separately formed core pack with an absorbent core enclosed between two casing layers. Although this may be a preferred way of incorporating an absorbent component into a pant article, an absorbent component may alternatively be incorporated utilising parts of the chassis structure as topsheet and/or backsheet.

All individual converting steps, such as bonding, cutting, folding, etc. are well known and described in the art and are not disclosed in detail herein. In the method in FIG. 1b, the first side edge 12b of the first panel web 8b is connected with the second side edge 13b of the second panel web 9b by means of a continuous bridging web 20b thereby forming a coherent chassis web 21b. In the example shown in FIG. 1b, the bridging web 20b has a width in the cross machine direction which is only sufficient to bridge the gap G between the first and second panel webs 8b, 9b and to enable the bridging web 20b to be attached to the first and second panel webs 8b, 9b along the first and second side edges 12b, 13b of the panel webs 8b, 9b. It should be understood that a continuous bridging web 20b may have a greater width than that shown in FIG. 1b and may overlap with all or part of one or both of the panel webs 8b, 9b in the cross machine direction CD.

The bridging web 20b may comprise or consist of a nonwoven web, a plastic film, or a laminate of two or more layers of such materials. The bridging web may also comprise elastic elements. It may be preferred that a nonwoven layer is placed such that it will form an inner surface of a pant article produced from the chassis web 21b.

Separately produced core packs 23b are laid down on the chassis web 21b in a spaced apart arrangement in the machine direction MD and with a longitudinal direction of the core packs 23b coinciding with the cross machine direction CD. The core packs 23b may be adhesively attached to the chassis web 21b or may be attached by any other suitable method as known in the art.

The core pack 23b comprises an absorbent core 24b enclosed between two casing layers: a liquid barrier layer 25b and a liquid pervious topsheet layer 26b. In the shown example the core pack 23b further comprises elastic elements 27b arranged between the casing layers 2b5, 26b in edge parts of the casing layers which protrudes outside the edges of the absorbent core 24b. The elastic elements 27b in the core pack 23b are optional components of the core pack 23b. The casing layers 25b, 26b may be chosen among any suitable backsheet materials and topsheet materials as known in the art. Likewise, the absorbent core 24b may be of any suitable construction, shape and size, as known in the art.

Leg openings 30b are cut out in the chassis web 1b between the core packs 23b using a cutting tool 31b. Thereafter the chassis web is folded along a centre line extending in the machine direction MD and side seam areas 40b are formed to delimit individual pant article blanks 49b between the side seam areas 40b. As schematically indicated in FIG. 1b, side seam areas 40b may be formed using an ultrasonic welding arrangement 41b or by any other suitable means, as set out herein.

Finally, individual pant articles 50b are formed by severing the chain of pant article blanks in the side seam areas 40b such that one part of each side seam area 40b forms a side seam 42b on a leading pant article and the other part of the side seam area 40b forms a side seam 43b on a trailing pant article 50b.

In the method illustrated in FIG. 1c, the first side edge 12c of the first panel web 8c is connected with the second side edge 13c of the second panel web 9c by means of multiple discrete bridging members 20c in the form of separately produced core packs 23c, thereby forming a coherent chassis web 21c. As shown in FIG. 1c, the bridging members 20c bridge the gap G between the first and second panel webs 8c, 9c and are attached to the first and second panel webs 8c, 9c on each side of the gap G. It should be understood that the bridging members 20c may have a different size and/or a different shape from that shown in FIG. 1c.

The core packs 23c are laid down on the chassis web 21c in a spaced apart arrangement in the machine direction MD and with a longitudinal direction of the core packs 23c coinciding with the cross machine direction CD. The core packs 23c may be adhesively attached to the first and second panel webs 8c, 9c or may be attached by any other suitable method as known in the art. It is to be understood that the provision of an absorbent core is optional to the methods disclosed herein and that the core packs 23c may be substituted by a bridging member without an absorbent core.

The core pack 23c comprises an absorbent core 24c enclosed between two casing layers: a liquid barrier layer 25c and a liquid pervious topsheet layer 26c. In the shown example the core pack 23c further comprises elastic elements 27c arranged between the casing layers 25c, 26c in edge parts of the casing layers which protrudes outside the edges of the absorbent core 24c. The elastic elements 27c in the core pack 23c are optional components of the core pack 23c. The casing layers 25c, 26c may be chosen among any suitable backsheet materials and topsheet materials as known in the art. Likewise, the absorbent core 24c may be of any suitable construction, shape and size, as known in the art.

Leg openings 30c are formed in the chassis web 1c by the spaces between the core packs 23c. After application of the bridging members 20c, the chassis web 1c is folded along a centre line extending in the machine direction MD and side seam areas 40c are formed to delimit individual pant article blanks 49c between the side seam areas 40c. As schematically indicated in FIG. 1c, side seam areas 40c may be formed using an ultrasonic welding arrangement 41c or by any other suitable means, as set out herein.

Finally, individual pant articles 50c are formed by severing the chain of pant article blanks in the side seam areas 40c such that one part of each side seam area 40c forms a side seam 42c on a leading pant article and the other part of the side seam area 40c forms a side seam 43c on a trailing pant article 50c.

It is to be understood that the shifted panel webs 8,9 obtained after the process steps shown in FIG. 1a may be converted into individual pant articles by processes differing from those illustrated in FIGS. 1b and 1c. If using a continuous bridging member as illustrated in FIG. 1b, the bridging member may have a greater width than shown in FIG. 1a and may overlap with a greater part of one or both of the panel webs and may even extend all the way to one or both of the cut edges. The pant articles as disclosed herein need not be absorbent articles. Accordingly, the application of absorbent cores is an optional process step. Furthermore, the process may include applying further elements such as leg elastic elements, raised barriers, fasteners at the side seams, etc.

FIG. 2 shows an absorbent pant article 50 which may be produced by a method as disclosed herein, such as by the method illustrated in FIG. 1c. An absorbent pant article produced according to the method in FIG. 1b, will have the same construction at the waist opening as the article produced by the method in FIG. 1c, but will have a different appearance at the leg openings and in the crotch portion due to the provision of a continuous bridging member between the front and rear panel webs.

The pant article is shown as it appears when worn with the side seams 42, 43 placed at the hips of the wearer. The pant article 50 has a waist opening 51 with a waist opening edge 52 and comprises a front panel 53 and a rear panel 63. The front panel 53 comprises a front panel material 54 originating from a front panel web being part of a chassis web as disclosed herein and having a front panel material upper edge 55 and a front panel material lower edge 12 and a front waistband 56 originating from the waistband portion of a front panel web being part of a chassis web as disclosed herein and having a front waistband edge 57. The front waistband 56 is attached in an overlapping configuration to a front waist edge portion of the front panel material 54. The rear panel 63 comprises a rear panel material 64 originating from a rear panel web being part of a chassis web as disclosed herein and having a rear panel material upper edge 65 and a rear panel material lower edge (not visible in FIG. 2) and a rear waistband 66 originating from the waistband portion of a rear panel web being part of a chassis web as disclosed herein and having a rear waistband edge 67. The rear waistband is attached in an overlapping configuration to a rear waist edge portion of the rear panel material 64. The waist opening edge 52 is a cut edge and comprises a front waist opening edge portion 52' and a rear waist opening edge portion 52". The front waist opening edge portion 52' comprises the front panel material edge 55 and the front waistband edge 57 and the rear waist opening edge portion 52" comprises the rear panel material edge 65 and the front waistband edge 67.

The cut waist opening edge 52 shown in FIG. 2 is a non-linear cut edge with a zig-zag shape. As disclosed herein, any alternative edge shape may be used such as a straight edge, a sinusoidal edge, etc. It may be preferred that the front and rear waist opening edge portions 52', 52" have the same shape such that the waist opening edge 52 has a uniform appearance. However, different front and rear cut edge shapes are also contemplated for the pant articles as disclosed herein.

The absorbent pant article 50 in FIG. 2 is shown with an absorbent core 23 which is enclosed between a liquid-impervious barrier sheet 25 and a liquid permeable topsheet 26. The liquid-impervious barrier sheet 25 has rectangular shape and the absorbent core 23 is hour-glass shaped.

The liquid-permeable topsheet 26 can consist of any material known for the purpose, such as a layer of nonwoven material, a perforated plastic film, net material, tow, or the like. The topsheet 26 can, of course, also consist of a laminate of two or more sheets of the same or different material.

The liquid-impervious barrier sheet 25 can consist of a liquid-impermeable plastic film, a nonwoven sheet which has been coated with a liquid barrier material, or some other flexible material sheet which has the ability to withstand liquid penetration. However, it can be advantageous if the liquid-impervious barrier sheet 25 is breathable, i.e. permits the passage of water vapour through the sheet 25.

The absorption core 23 can be made up of absorbent material, such as cellulose fluff pulp, tissue, absorbent foam, etc. It is also possible for the absorption core to contain superabsorbents, i.e. polymer materials which are able to absorb body fluid corresponding to many times their own weight and form a hydrogel. Superabsorbents are usually present in the form of particles, but fibres, flakes, granules and films are also available. Moreover, the absorption core 23 can comprise non-absorbent components such as stiffening elements, shaping elements, binders, etc. Various types of liquid-receiving porous structures such as fibre wads, open-cell foam or the like can also be included in the core.

It is conventional in absorbent articles to have an absorbent core comprising layers of different properties with respect to liquid receiving capacity, liquid distribution capacity and storage capacity. The thin absorbent bodies, which are common in for example baby diapers and incontinence articles, often comprise a compressed mixed or layered structure of cellulosic fluff pulp and superabsorbent polymers. The size and absorbent capacity of the absorbent core may be varied to be suited for different uses such as for infants or for adult incontinent persons.

The absorbent core may further include an acquisition distribution layer placed on top of the primary absorbent body and which is adapted to quickly receive and temporarily store discharged liquid before it is absorbed by the primary absorbent core. Such acquisition distribution layers are well known in the art and may be composed of porous fibrous waddings or foam materials.

As set out herein, the absorbent core may be of different shape and may have a different size from that shown in FIG. 2. An absorbent core may also have been incorporated in the article in other ways than as core pack.

With reference to FIG. 3, there is shown a cross-section through the front panel 53 at the waist opening edge 52. The front panel material 54 is formed from a first base material which is a bi-laminate of an elastic film layer 76 and a nonwoven layer 75 and a second base material which is a single-layer nonwoven material 74. In the embodiment shown in FIG. 3, the waistband 56 is a laminate structure of the base material layers 74, 75, 76 with a waistband of closely spaced elongated elastic elements 73 attached between the film layer 76 of the first base material and the nonwoven layer 74 of the second base material. The illustrated waistband construction is intended only as a non-limiting example, and it is to be understood that any suitable materials and material combinations may be used for the waistband and the front panel material, as disclosed herein.

As set out herein, the front and rear panels 53, 63 of the absorbent pant article 50 may comprise or consist of a first elastic material, and the front waist band and the rear waist band 56, 66 may comprise or consist of a second elastic material, whereby the overlapping portions of the front and rear panels 53, 63 and the front and rear waistbands 56, 66 form an elastic waist zone 80 at the waist opening edge 52. The elastic waist zone 80 comprises both the first elastic material and the second elastic material. The elastic waist zone 80 has a width which is determined by the width of the waistbands. The width of the elastic waist zone 80 is the extension of the waist zone perpendicular to the waist opening edge 52 corresponding to the cross machine direction during production of the absorbent pant article 50. The width of the waistband may be from 5 mm to 100 mm, such as from 5 mm to 50 mm, or from 5 mm to 40 mm. In FIG. 3, the first elastic material is exemplified by an elastic film layer 76 and the second elastic material is exemplified by elongated elastic elements 73. The production method as disclosed herein allows the first and second elastic materials to be separate selected to provide the elastic waist zone 80 with the desired elastic properties.

As a result of the waist edge having been formed by simultaneously cutting through both of the base materials and the elastic component, the cut edge 55 on the front panel material 54 is coterminous with the front waistband edge 57 on the front waistband 56.

Description of Test Method

Elasticity Test

The method measures the behaviour of an elastic material at cycles of repeated load and unload. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:
Crosshead speed: 500 mm/min
Clamp distance: 50 mm
Preload: 0.05 N The sample is placed in the clamps according to the marks and it is made sure that the sample I centred and fastened perpendicularly in the clamps. The tensile tester is started and three cycles between 0 and the predetermined elongation equal to the highest defined $1^{st}$ load are performed. Before the last cycle, the sample is relaxed for 1 minute, then the permanent elongation is measured by stretching the sample until a force of 0.1 N is detected and the elongation is read.

An elastic material is defined as a material having a permanent elongation after relaxation of less than 10% after the material has been subjected to an elongation of 30% in the test above. An elongation of 30% means an elongation to a length that is 30% longer than the initial length of the sample.

A non-elastic material has a permanent elongation after relaxation of more than 10% after having been subjected to an elongation of 30%.

The invention claimed is:

1. A method for producing a chassis web for a disposable pant article, the method comprising:
    feeding a first continuous elastic base web in a machine direction, said first continuous elastic base web having first and second side edges extending in said machine direction;
    attaching a continuous elastic waistband component to said first continuous elastic base web in an attachment area, said attachment area extending in said machine direction and being arranged between said first and said second side edges of said first continuous elastic base web, wherein the first continuous elastic base web comprises, in order from the first side edge to the second side edge: a first panel portion, the continuous elastic waistband component, and a second panel portion;
    attaching a second continuous base web to said first continuous elastic base web and said continuous elastic waistband component, covering at least said continuous waistband component, said second continuous base web having first and second side edges extending in said machine direction thereby forming a compound base web having first and second side edges, said attachment area being spaced apart from at least one of said first and said second side edges of said compound base web;
    severing said compound base web by cutting along a cutting line extending through said attachment area in said machine direction thereby creating a first panel web having a first side edge and comprising the first panel portion and a first waistband portion and a second panel web having a second side edge and comprising the second panel portion and a second waistband portion, said first panel web and said second panel web extending in said machine direction with said first and second waistband portions facing each other in a side-by-side arrangement;
    shifting positions of said first panel web and said second panel web in a cross machine direction perpendicular to said machine direction, thereby bringing said first and said second panel webs into an arrangement with first and second cut edges facing away from each other in said cross machine direction and with said first and second side edges of said first and second panel webs facing each other in said cross machine direction;
    directly or indirectly connecting said first side edge of said first panel web with said second side edge of said second panel web thereby forming a coherent chassis web, wherein the first continuous elastic base web becomes a garment facing portion of the disposable pant article.

2. The method according to claim 1, wherein the first continuous elastic base web comprises an elastic film.

3. The method according to claim 1, wherein the elastic waistband component and the first continuous elastic base web are held stretched from 50% to 600% in the machine direction when attaching the waistband component to the first continuous elastic base web.

4. The method according to claim 1, wherein the elastic waistband component is stretch-bonded to the first continuous elastic base web.

5. The method according to claim 1, wherein the elastic waistband component is stretch to a same degree as the first continuous elastic base web when attaching the elastic waistband component to the first continuous elastic base web.

6. The method according to claim 1, wherein the elastic waistband component is stretch to a different degree as the first continuous elastic base web when attaching the elastic waistband component to the first continuous elastic base web.

7. The method according to claim 1, wherein the elastic waistband component comprises threads.

8. The method according to claim 1, wherein the cutting line extending through said attachment area in said machine direction is non-linear.

9. The method according to claim 1, wherein said cutting line has an undulating shape.

10. The method according to claim 1, wherein said first and/or said second continuous base web comprises a bi-laminate web comprising a nonwoven layer and an elastic layer.

11. The method according to claim 1, wherein the elastic waistband component and the first continuous elastic base web are held stretched in the machine direction when attaching the waistband component to the first continuous elastic base web.

12. The method according to claim 1, wherein the first side edge of said first panel web with said second side edge of said second panel web are connected to each other with a bridging material.

* * * * *